(12) United States Patent
Greenberg et al.

(10) Patent No.: US 7,097,775 B2
(45) Date of Patent: Aug. 29, 2006

(54) COATED MICROFLUIDIC DELIVERY SYSTEM

(75) Inventors: Robert J. Greenberg, Los Angeles, CA (US); Brian V. Mech, Stevenson Ranch, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

(21) Appl. No.: 10/096,183

(22) Filed: Mar. 11, 2002

(65) Prior Publication Data

US 2003/0080085 A1 May 1, 2003

Related U.S. Application Data

(63) Continuation-in-part of application No. 10/046,458, filed on Oct. 26, 2001.

(51) Int. Cl.
*B23P 15/00* (2006.01)

(52) U.S. Cl. .................. 216/2; 216/39; 604/290.1
(58) Field of Classification Search ............ 216/2, 216/39, 56; 604/19, 890.1, 891.1, 892.1; 436/174, 518; 435/14, 285.2, 288.4; 422/68.1, 422/102, 104; 117/103, 108
See application file for complete search history.

(56) References Cited

U.S. PATENT DOCUMENTS 6,527,762 B1 * 3/2003 Santini et al. ........... 604/890.1
6,551,838 B1 * 4/2003 Santini et al. ............. 436/174

OTHER PUBLICATIONS

D.M. Gruen, et al. "Buckyball Microwave Plasmas: Fragmentation and Diamond Film Growth", J. Appl. Phys., 75(3) 1758–63 (1994).

D.M. Gruen, "Nanocrystalline Diamond Films" Annu. Rev. Mater. Sci., 29 211–59 (1999).

Mech, et al., "Accelerated Corrosion Tests on Silicon Wafers for Implantable Medical Devices", Proc. of 198th Electrochemical Society Meeting, Oct. 2000, 363.

G. Kovacs, Micromachined Transducers Sourcebook, Cpt. 9, Microfluidic Devices, 1998, 779–882.

S. K. Cho, S. Fan, H. Moon, and C. Kim, "Towards Digital Microfluidic Circuits: Creating, Transporting, Cutting and Merging Liquid Droplets by Electrowetting–Based Actuation," Proc. IEEE 15th Intl. Conference on Micro Electro Mechanical Systems, Las Vegas, Nevada, Jan. 20–24, 2002, 32–35.

* cited by examiner

*Primary Examiner*—William A. Powell
(74) *Attorney, Agent, or Firm*—Tomas Lendvai; Scott Dunbar

(57) ABSTRACT

A microfluidic delivery system substrate is coated with ultra-nanocrystalline diamond (UNCD) or with a thin ceramic film, such as alumina or zirconia, that is applied by ion-beam assisted deposition; assuring that the device is impermeably sealed, to prevent the substrate from being dissolved by hostile environments and to protect the molecules from premature release or undesired reaction with hostile environments. The UNCD coating may be selectively patterned by doping to create electrically conductive areas that can be used as an electrically activated release mechanism for drug delivery. The UNCD coating provides a conformal coating, of approximately uniform thickness, around sharp corners and on high aspect-ratio parts, assuring impermeability and strength despite the need to coat difficult shapes. The microfluidic delivery system is suitable for use as an iontophoresis device, for transport of molecule, having a substrate, a reservoir in the substrate for containing the molecules.

45 Claims, 6 Drawing Sheets

COATED MICROFLUIDIC DELIVERY SYSTEM

CROSS REFERENCE TO RELATED APPLICATION

This application is a continuation-in-part of patent application Ser. No. 10/046,458, filed on Oct. 26, 2001, entitled "IMPLANTABLE MICROFLUIDIC DELIVERY SYSTEM USING ULTRA-NANOCRYSTALLINE DIAMOND COATING."

FEDERALLY SPONSORED RESEARCH

This invention was made with government support under grant No. R24EY12893-01, awarded by the National Institutes of Health. The government has certain rights in the invention.

FIELD OF THE INVENTION

The present invention relates to a microfluidic delivery system that is coated with an inert and impermeable thin film and more particularly to controlled time of release and rate of release, welled drug delivery devices, which may also be implantable in a living body.

BACKGROUND OF THE INVENTION

As people strive to create complete fluidic systems in miniaturized formats, micromachining becomes more important. A broad variety of materials is available for fabricating the systems or their components, including glasses, plastics/polymers, metals, ceramics and semiconductors. To take full advantage of the available microfluidic advances, one must deal with significant additional issues, such as packaging, interfaces between components, and testing. Integrated microfluidic systems may consist of pumps, valves, channels, reservoirs, cavities, reaction chambers, mixers, heaters, fluidic interconnects, diffusers, and nozzles. Applications of microfluidic systems include chemical analysis; biological and chemical sensing; drug delivery; molecular separation; amplification, sequencing or synthesis of nucleic acids; environmental monitoring; and many others. Potential benefits include reduced size, improved performance, reduced power consumption, disposability, integration of control electronics, and lower cost.

The device body structure of the microfluidic device typically comprises an aggregation of separate parts, e.g., capillaries, joints, chambers, layers, etc., which when appropriately mated or joined together, form the microfluidic device. Typically, the microfluidic devices comprise a top portion, a bottom portion, and an interior portion. The bottom portion typically comprises a solid substrate that is substantially planar in structure with at least one substantially flat upper surface. A variety of substrate materials may be employed as the bottom portion. Typically, because the devices are microfabricated, substrate materials generally are selected based upon their compatibility with known microfabrication techniques, e.g., photolithography, wet chemical etching, laser ablation, air abrasion, techniques, injection molding, embossing, and other techniques. The substrate materials are also generally selected for their compatibility with the full range of conditions to which the microfluidic devices may be exposed, including extremes of pH, temperature, salt concentration, and application of electric fields.

Accordingly, in some preferred aspects, the substrate material may include materials normally associated with the semiconductor industry in which such microfabrication techniques are regularly employed, including, e.g., silica based substrates such as glass, quartz, silicon or polysilicon, as well as other substrate materials, such as gallium arsenide. In the case of semiconductive materials, it is often desirable to provide an insulating coating or layer, e.g., silicon oxide, over the substrate material, particularly where electric fields are to be applied.

In addition, it is known that the substrate materials will comprise polymeric materials, e.g., plastics, such as polymethylmethacrylate, polycarbonate, polytetrafluoroethylene, polyvinylchloride, polydimethysiloxane, and polysulfone. Such substrates are readily manufactured from microfabricated masters, using well-known molding techniques, such as injection molding, embossing or stamping, or by polymerizing the polymeric precursor material within the mold. Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic systems, e.g., provide enhanced fluid direction.

The channels and/or chambers of the microfluidic devices are typically fabricated into the upper surfaces of the substrate, or bottom portion, using the above described microfabrication techniques, as microscale grooves or indentations. The lower surface of the top portion of the microfluidic device, which top portion typically comprises a second planar substrate, is then overlaid upon and bonded to the surface of the bottom substrate, sealing the channels and/or chambers interior portion) of the device at the interface of these two components. Bonding of the top portion to the bottom portion may be carried out using a variety of known methods, depending upon the nature of the substrate material. For example, in the case of glass substrates, thermal bonding techniques may be used which employ elevated temperatures and pressure to bond the top portion of the device to the bottom portion. Polymeric substrates may be bonded using similar techniques, except that the temperatures used are generally lower to prevent excessive melting of the substrate material. Alternative methods may be used to bond polymeric parts of the device together, including acoustic welding techniques, or the use of adhesives, e.g., UV curable adhesives.

Microfluidic systems are highly useful in medical diagnostics or drug delivery. Microfluidic delivery systems, as the microchip drug delivery devices of Santini, et al. (U.S. Pat. No. 6,123,861) and Santini, et al. (U.S. Pat. No. 5,797,898) or fluid sampling devices, must be impermeable and they must be biocompatible. The devices must not only exhibit the ability to resist the aggressive environment present in the body, but must also be compatible with both the living tissue and with the other materials of construction for the device itself. The materials are selected to avoid both galvanic and electrolytic corrosion. See U.S. Pat. Nos. 5,725,017; 5,797,898; 5,876,675; 6,123,861; and 6,154,226, each of which is incorporated in its entirety by reference herein. The digital microfluidic circuits of Cho, et al. also require compatible reservoirs to contain fluids which are processed by their novel electrowetting techniques.

In microchip drug delivery devices, the microchips control both the rate and time of release of multiple chemical substances and they control the release of a wide variety of molecules in either a continuous or a pulsed manner. A material that is impermeable to the drugs or other molecules to be delivered and that is impermeable to the surrounding fluids is used as the substrate. Reservoirs are etched into the substrate using either chemical etching or ion beam etching techniques that are well known in the field of microfabrication. Hundreds to thousands of reservoirs can be fabricated on a single microchip using these techniques.

Microfluidic systems, in addition to being highly useful in medical diagnostics, are also useful in environmental monitoring, biological food testing, chemical sensing and analysis. Current efforts on the fabrication of microfluidic systems and fluidic technologies have focused on individual component development. Components such as pumps, valves, and fluidic channels are at various stages of development. Mastrangelo, et al. (U.S. Pat. No. 6,136,212) discuss the use of protective barrier layers. U.S. Pat. No. 6,136,212, is incorporated in its entirety by reference herein The physical properties of the release system control the rate of release of the molecules, e.g., whether the drug is in a gel or a polymer form.

The reservoirs may contain multiple drugs or other molecules in variable dosages. The filled reservoirs can be capped with materials either that degrade or that allow the molecules to diffuse passively out of the reservoir over time. They may be capped with materials that disintegrate upon application of an electric potential. Release from an active device can be controlled by a preprogrammed microprocessor, remote control, or by biosensor. Valves and pumps may also be used to control the release of the molecules.

A reservoir cap can enable passive timed release of molecules without requiring a power source, if the reservoir cap is made of materials that degrade or dissolve at a known rate or have a known permeability. The degradation, dissolution or diffusion characteristics of the cap material determine the time when release begins and perhaps the release rate.

Alternatively, the reservoir cap may enable active timed release of molecules, requiring a power source. In this case, the reservoir cap consists of a thin film of conductive material that is deposited over the reservoir, patterned to a desired geometry, and that serves as an anode. Cathodes are also fabricated on the device with their size and placement determined by the device's application and method of electrical potential control. Known conductive materials that are capable of use in active timed-release devices that dissolve into solution or form soluble compounds or ions upon the application of an electric potential, including metals, such as copper, gold, silver, and zinc and some polymers.

When an electric potential is applied between an anode and cathode, the conductive material of the anode covering the reservoir oxidizes to form soluble compounds or ions that dissolve into solution, exposing the molecules to be delivered to the surrounding fluids. Alternatively, the application of an electric potential can be used to create changes in local pH near the anode reservoir cap to allow normally insoluble ions or oxidation products to become soluble. This allows the reservoir cap to dissolve and to expose the molecules to be released to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip.

An alternative method of drug delivery, wherein microfluidic devices are employable, involves devices for transdermal delivery or transport of therapeutic agents through iontophoresis. "Iontophoresis" refers to (1) the delivery of charged drugs or molecules by electromigration, (2) the delivery of uncharged drugs or molecules by the process of electroosmosis, (3) the delivery of charged drugs or molecules by the combined processes of electromigration and electroosmosis, and/or (4) the delivery of a mixture of charged and uncharged drugs or molecules by the combined processes of electromigration and electroosmosis. See U.S. Pat. Nos. 5,681,484; 5,846,396; 6,317,629; and 6,330,471, each of which is incorporated in its entirety by reference herein.

Iontophoretic devices for delivering ionized drugs through the skin have been known since the early 1900's. Deutsch (U.S. Pat. No. 410,009 (1934)) describes an iontophoretic device that overcame disadvantages of early devices. In presently known iontophoresis devices, at least two electrodes are used. Both of these electrodes are disposed to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is negatively charged, then the negative electrode (the cathode) will be the active electrode and the positive electrode (the anode) will serve to complete the circuit.

Existing iontophoresis devices generally require a reservoir or source of the drug or other molecule, preferably an ionized or ionizable species that is to be iontophoretically delivered or introduced into the body. Such reservoirs are connected to the anode or the cathode of an iontophoresis device to provide a fixed or renewable source of one or more desired drugs or molecules.

Such iontophoresis devices may also be implanted in living tissue. Whether implanted or not, the devices must be compatible with the drugs or other molecules that they contain and must be compatible with the living tissue.

One solution to achieving biocompatibility, impermeability, and galvanic and electrolytic compatibility for an implanted device is to encase the device in a protective environment. It is well known to encase implantable devices with glass or with a covering of ceramic or metal. Davidson (U.S. Pat. No. 5,562,730), Schulman, et al. (U.S. Pat. No. 5,750,926), Cogan (U.S. Pat. No. 5,755,759) and Schulman, et al. (U.S. Pat. No. 6,259,937 B1) offer examples of this technique. See also, U.S. patent application Ser. No. 09/882,712, Publication No.: US2001/0039374 A1. U.S. Pat. Nos. 5,562,730; 5,750,926; 6,259,937 B1; and U.S. patent application Ser. No. 09/882,712, Publication No.: US2001/0039374 A1, each of the aforementioned U.S. Patents is incorporated in its entirety by reference herein.

It is known to coat microfluidic devices to increase compatibility with biological fluids (Kovacs, Micromachined Transducers Sourcebook, p 803). Kovacs reports that researchers sealed channels using a plasma-enhanced chemical vapor deposition technique to deposit amorphous, hydrogenated silicon carbide film as a deposited thin-film layer. Kovacs reports that researchers vapor-deposited an organic coating on channels to achieve compatibility with biological compounds. Cogan (U.S. Pat. No. 5,755,759) coats a biomedical device with a low permeability to water, electrically resistive thin film of amorphous silicon oxycarbide.

Santini, et al. (U.S. Pat. No. 6,123,861) discuss the technique of encapsulating a non-biocompatible material in a biocompatible material, such as poly(ethylene glycol) or polytetrafluoroethylene-like materials. They also disclose the use of silicon as a strong, non-degradable, easily etched substrate that is impermeable to the molecules to be delivered and to the surrounding living tissue. The use of silicon allows the well-developed fabrication techniques from the electronic microcircuit industry to be applied to these substrates.

It is well known, however, that silicon is dissolved when implanted in living tissue or in saline solution. Zhou, et al. report that the calculated corrosion rates are 0.005, 0.077, 0.440 and 0.690 mils per year for samples of silicon soaked in bicarbonate buffered saline at 23°, 37°, 57° and 77° C.

A method of providing microfluidic devices that are impermeable and inert to the molecules being contained therein and that resist the often hostile environments in which they are placed is needed.

SUMMARY OF THE INVENTION

A microfluidic delivery system for the transport of molecules comprises a substrate; a reservoir in the substrate for containing the molecules; a fluid control device controlling release of molecules from the reservoir; and a thin film inert impermeable coating applied to the substrate.

A microfluidic delivery system for release of molecules having a substrate; at least one reservoir in the substrate that is suitable to contain the molecules; at least one reservoir having at least one reservoir cap positioned on the reservoir over the molecules, where release of the molecules from the reservoir is controlled by the reservoir cap; and where a substrate is coated with a thin film of ultra-nanocrystalline diamond deposited on the microfluidic delivery system where the thin film forms a biocompatible impermeably sealed substrate.

A method of fabricating a microfluidic delivery system for release of molecules having at least one reservoir containing the molecules for release, comprising providing a substrate; depositing a thin inert and impermeable film coating; filling the reservoirs with molecules to be release into living tissue; and capping the reservoirs with a cap material which retains the molecules.

An iontophoresis device, for the transport of molecules, having a substrate; at least one reservoir in the substrate for containing the molecules; a fluid control device controlling release of the molecules from the reservoir; and a thin film inert impermeable coating applied to the substrate.

The novel features of the invention are set forth with particularity in the appended claims. The invention will be best understood from the following description when read in conjunction with the accompanying drawings.

OBJECTS OF THE INVENTION

It is an object of the invention to provide an ion-beam assisted deposited coating on a microfluidic delivery system.

It is an object of the invention to provide an ultra-nanocrystalline diamond coated microfluidic delivery system substrate that is impermeably sealed and inert for implantation in a living body.

It is an object of the invention to provide an ultra-nanocrystalline diamond coated microfluidic delivery system substrate that has a uniform thickness coating around corners such that the coating maintains its impermeable sealing capability.

It is an object of the invention to provide an ultra-nanocrystalline diamond coated microfluidic delivery system substrate that has electrically conductive areas that are patterned to provide a mechanism for electrically activated release.

It is an object of the invention to provide a coated microfluidic delivery device that is suitable for iontophoretic transport of molecules.

Other objects, advantages and novel features of the present invention will become apparent from the following detailed description of the invention when considered in conjunction with the accompanying drawing.

DETAILED DESCRIPTION OF THE PREFERRED EMBODIMENTS

Figure 2:
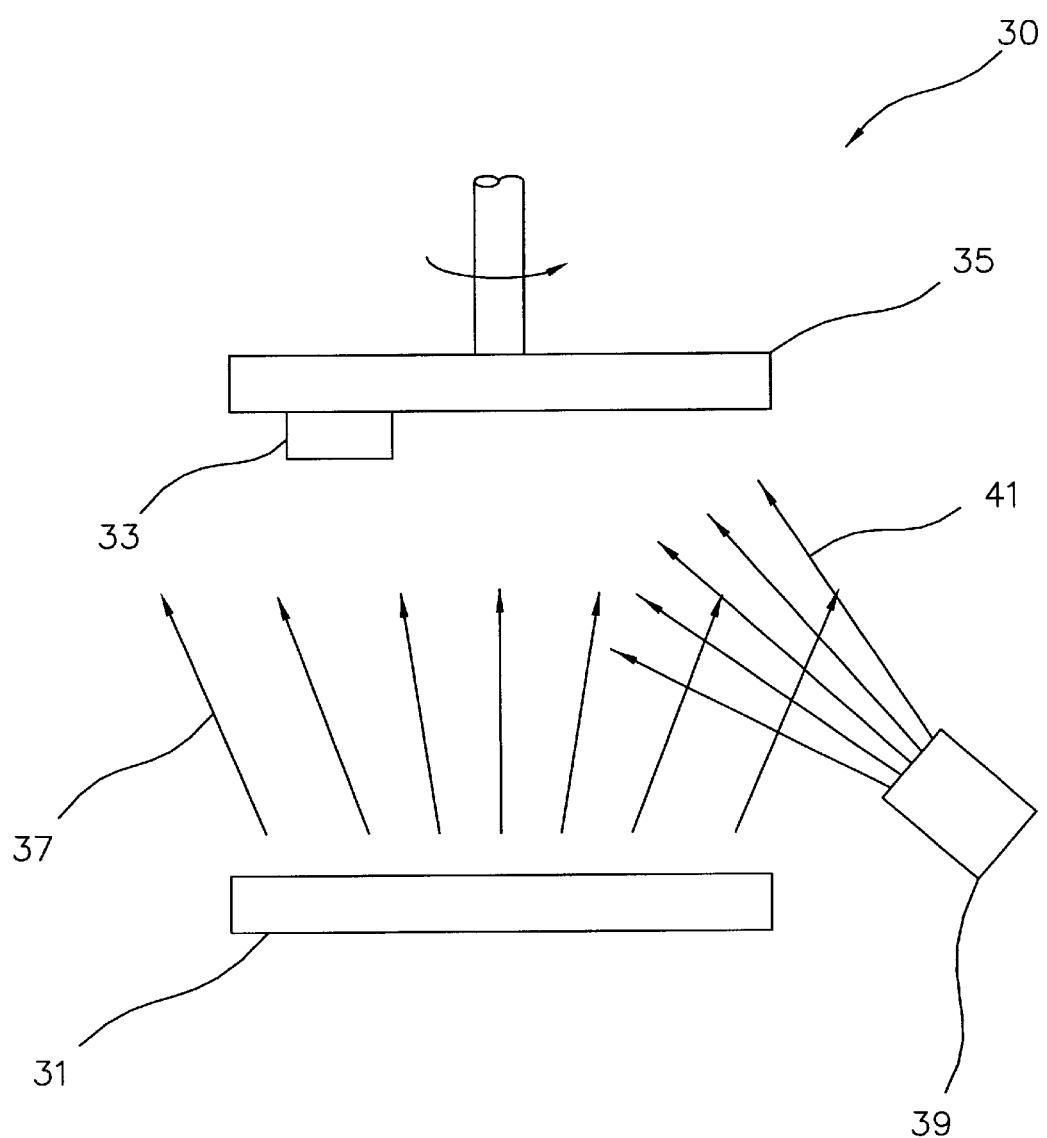
FIG. 2 illustrates a schematic representation of the ion-beam assisted deposition process.

The instant invention utilizes thin coatings of ultra-nanocrystalline diamond (UNCD) or other ceramic materials, where the other ceramic materials are deposited by ion-beam assisted deposition (IBAD) techniques, generally illustrated in FIG. 2. It is known that UNCD coatings are an improvement over diamond thin films, diamond-like-carbon, and nanocrystalline diamond, in that the UNCD coatings are impermeable in coatings as thin as 5 microns.

Ion-enhanced evaporative sputtering applied coatings, of alumina or zirconia, for example, are impermeable in coatings of approximately 10 microns thickness. See U.S. Pat. No. 6,043,437, which is incorporated herein by reference its entirety. IBAD coatings also offer electrically insulating characteristics in salt water, for example, of less than about $10^{-6}$ amps/cm$^2$. IBAD applied coatings can be patterned by conventional techniques. IBAD is a line-of-sight deposition process that achieves very dense coatings in a cost-affordable process.

IBAD 30, as shown in FIG. 2, is a vacuum-deposition process that combines physical vapor deposition and ion beam bombardment to achieve a superior coating. The electron-beam evaporator 31 generates a vapor of coating atoms 37 which are deposited on a substrate 33. The substrate 33 is mounted on a rotating substrate holder 35 to assure that the coating is applied uniformly to the substrate 33. A distinguishing feature of IBAD is that the coating is bombarded with energetic ions 41 as it is being deposited on the substrate 33. The energetic ions are generated by the ion source 39. Alumina or yttria-stabilized zirconia may be employed as the coating material. This method allows biaxially textured layers of high quality to be produced that permit deposition of films for example with very good properties. IBAD coatings of alumina, zirconia, or other ceramic materials are well known improvements over known vapor deposition techniques because they are impermeable in coatings as thin as 10 microns. The IBAD coatings are stronger than other vapor deposited coatings and can be deposited by line-of-sight at low substrate temperatures, which is necessary when using an organic substrate.

If the application for the microfluidic device involves implantation in living tissue, then either UNCD or ceramic deposited by IBAD provides a protective and biocompatible surface coating.

Figure 1:
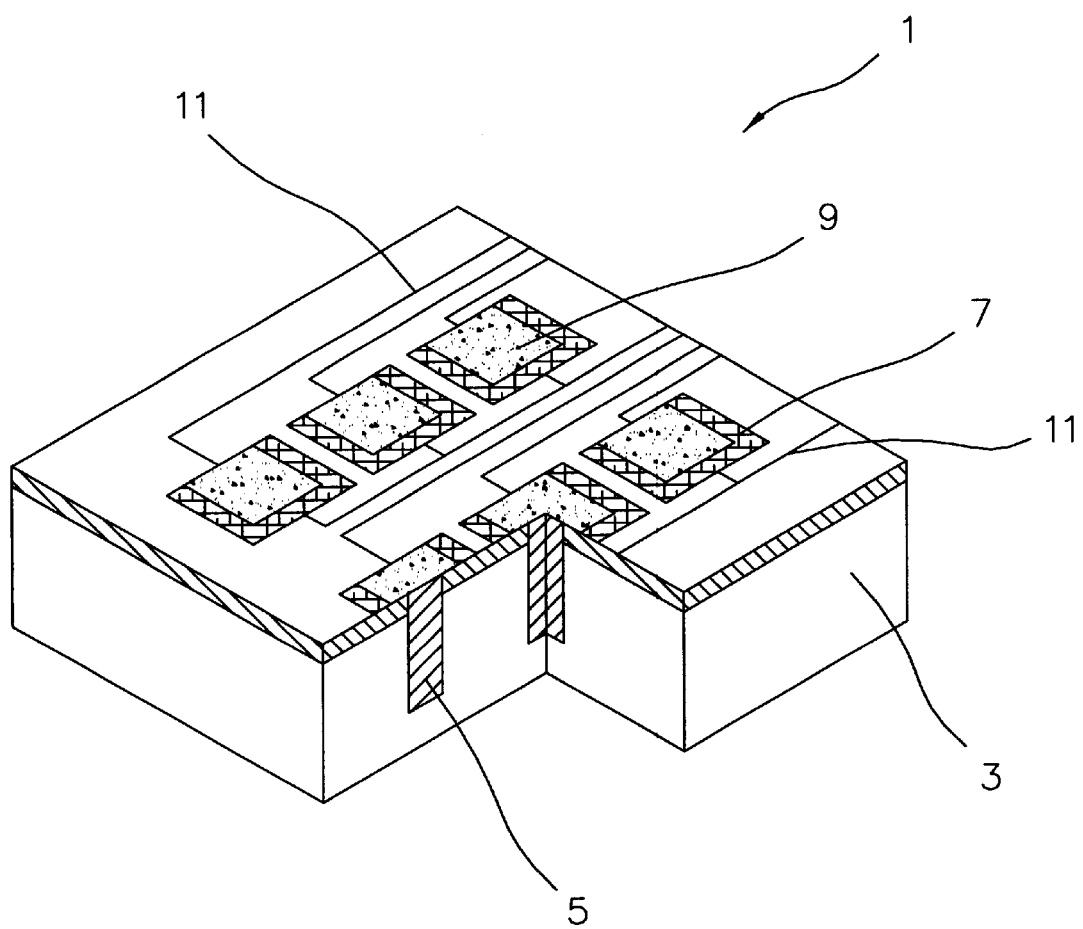
FIG. 1 illustrates a perspective view of the microfluidic delivery system.

Implantable microfluidic delivery systems generally are comprised of a microchip 1, as shown in FIG. 1. The microchip 1 must be biocompatible and impermeable to assure that the drug or other molecule 5 contained in the reservoirs of the substrate 3 are protected from the living tissue of the body and to retain the drug or other molecule 5 until the desired release time.

It is known to fabricate reservoirs, by conventional microchip techniques, in the substrate of the delivery device from silicon. Silicon is dissolved when exposed, long term, to living tissue in a living body, unless coated with a biocompatible coating. An ultra-nanocrystalline diamond (UNCD) coating 13 exhibits excellent mechanical, electrical, and electrochemical properties. Using a thin film coating deposition process, such as that disclosed by Gruen and Krauss (U.S. Pat. No. 5,772,760), yields a UNCD coating that is inherently low in porosity, electrically nonconductive and biocompatible. U.S. Pat. No. 5,772,760 is incorporated herein by reference in its entirety. UNCD coatings as thin as 40 nm have demonstrated excellent impermeability properties. The UNCD thin film coating 13 is conformal when applied to complex or high aspect-ratio shapes.

Characteristics of this UNCD coating 13 that make it particularly well suited to the present invention are:

uniform morphology resulting in a very high bulk density, highly conformal and able to cover very high-aspect ratio features uniformly, electrical properties can be controlled by varying the deposition parameters, so as to make selected areas electrically conductivity, low-temperature deposition thereby avoiding damage to electrical and passive components, and easily patternable via selective seeding, photolithography, or oxygen etching.

Unique UNCD coating 13 properties are not all present in any other single coating candidate for microchip drug delivery devices. Candidate coatings include conventional chemical vapor deposited diamond thin films, diamond-like carbon, or SiC. However, none of these coatings offers impermeability in thin coatings that are applied at low temperature and that are deposited by a none-line-of-sight method, as does UNCD. The UNCD coating 13 possesses these characteristics:

(a) extremely low surface roughness (20–30 nm), approximately independent of film thickness up to approximately 10 µm thickness;

(b) extremely good conformality when deposited on high aspect-ratio features;

(c) extremely low coefficient of friction;

(d) high hardness, fracture toughness, flexural strength, and wear life, (e) low electrical conductivity, but can be doped to become conductive, and (f) excellent resistant to degradation in living tissue environments.

The UNCD coating 13 consists primarily of phase pure randomly oriented diamond crystallites. UNCD coatings are grown using a microwave plasma chemical vapor deposition technique involving a $C_{60}$/Ar or $CH_4$/Ar chemistry, which provides $C_2$ dimers as the main growth species that insert directly into the growing diamond lattice with a low energy barrier. The limited amount of atomic hydrogen in the plasma leads to a very high re-nucleation rate (~$10^{11}$ cm$^{-2}$ sec$^{-1}$). This results in the UNCD coatings 13 with 2 to 5 nm grain size and 0.4 nm grain boundaries that provide the unique properties described herein. In addition, the low activation energy for $C_2$ species incorporation into the growing film yields the UNCD coating 13 at temperatures as low as approximately 350° C. This temperature is very low compared to many conventional coating processes, such as glass encapsulation or chemical vapor deposition.

Microfluidic delivery systems that are placed in a hostile environment, such as those that are implanted in a living body, benefit from a UNCD coating 13 that, in addition to biocompatibility, corrosion resistance, and impermeability, can be patterned to form electrically conductive electrodes. Patterning is done by selective doping of the UNCD coating 13 to convert the normally electrically insulating UNCD 13 to an electrical conductor. The electrical conductors 11 are formed in this manner, as is the anode electrode reservoir cap 9. These electrode caps 9 are formed as covers on the drug 5 or other molecule-containing reservoirs. Upon application of an electric current along the electrical conductors 11, through the cathode electrodes 7 and into the anode electrode reservoir cap 9 anode electrode reservoir cap 9 disintegrates to expose the drug or other molecule 5 to the living tissue, thus allowing the drug or other molecule 5 to enter the body. It is obvious that the device may equally well be used to deliver reagents or to act as a diagnostic agent in addition to delivering drugs.

The inert nature of a very thin coating of UNCD 13 was demonstrated by the present inventors. A silicon substrate coated with 40 nm of UNCD coating 13 was exposed to silicon etchant having a composition of 67% $HNO_3$ and 33% HF, by volume. The etchant was placed drop-wise on the UNCD coating 13, where it was allowed to stand at 60° C. for one-hour. The coating had been unaffected when observed microscopically at 1000× after this exposure.

Therefore, the UNCD coating 13 may be used as part of a biocompatible and impermeable microchip drug delivery packaging process to isolate the substrate 3, which is typically silicon, and to isolate the drug or other molecule 5 from the tissue and fluids that are present in the living tissue. In this manner, the substrate 3 is protected from the living tissue and the drug or other molecule 5 is maintained free from attack by either the silicon or the living tissue.

The UNCD coating 13 on an integrated circuit is "conformal", which means that the coating has a uniform thickness as the coating follows the contours of the device. Achieving a conformal coating on high aspect-ratio parts and around sharp corners on these devices is a particular challenge for thin films that are deposited by other means. UNCD coating 13 uniformly covers all aspects of the intricately machined substrate 3 including the multiplicity of reservoirs.

Figure 3:
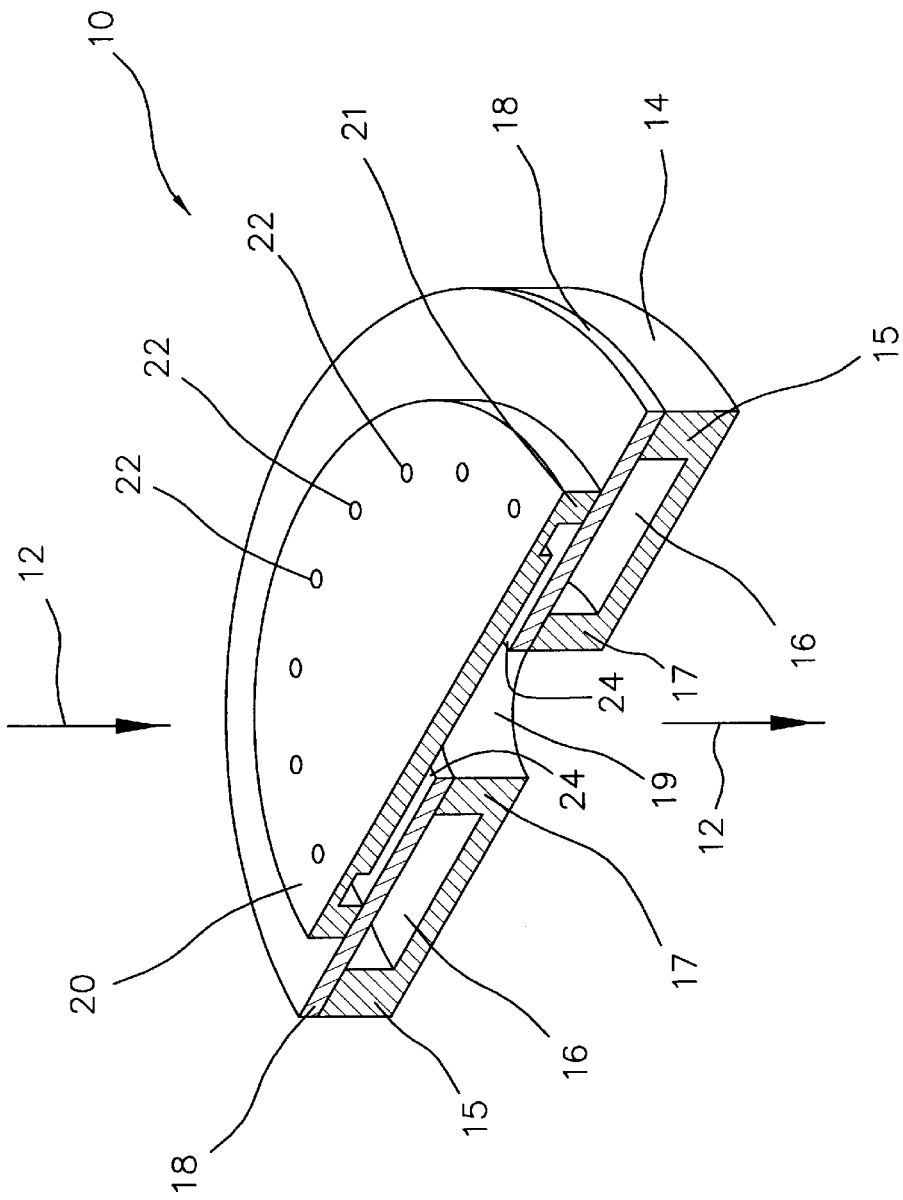
FIG. 3 illustrates an in-line pressure check valve.
Figure 4:
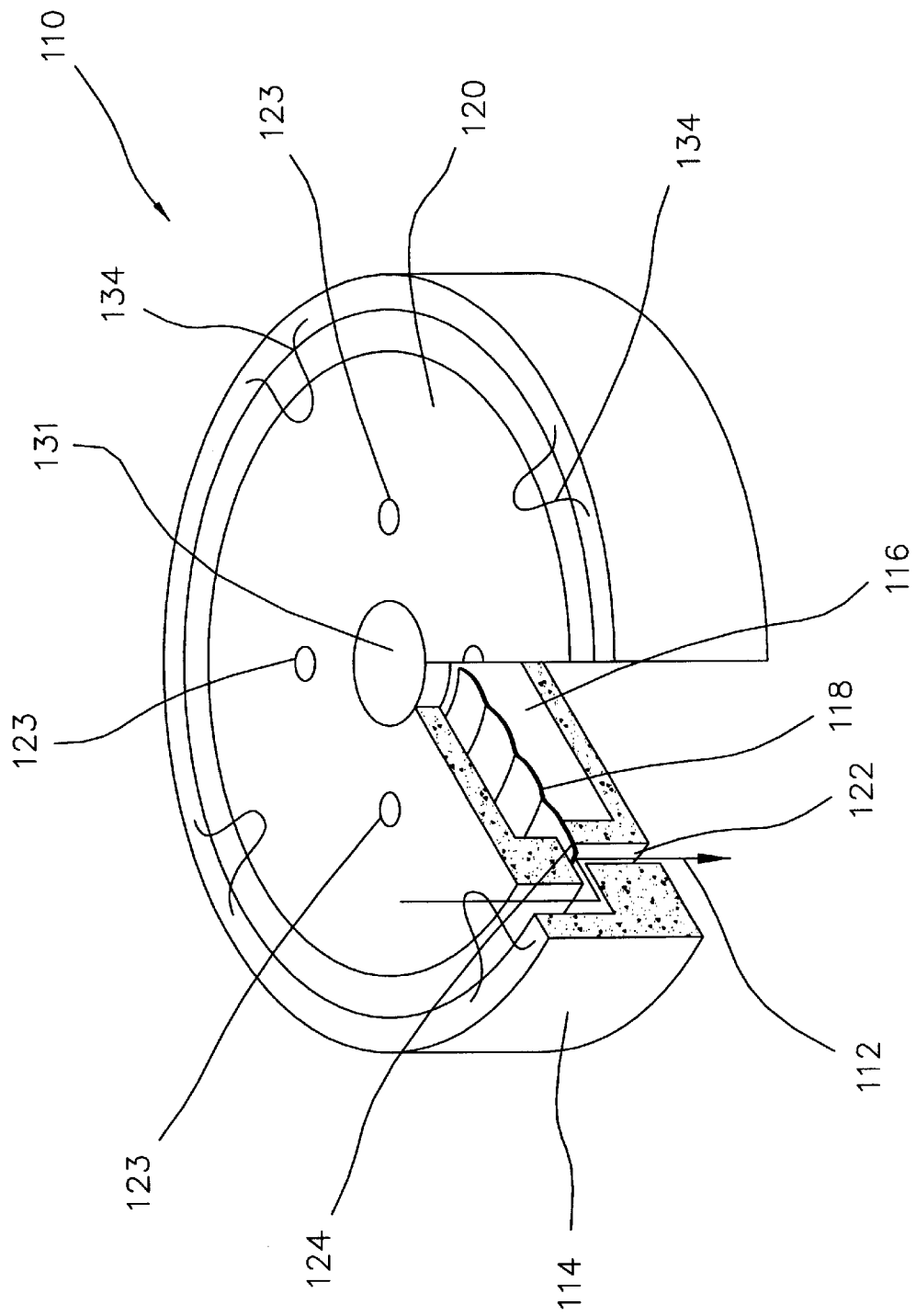
FIG. 4 illustrates a pressure valve.
Figure 5:
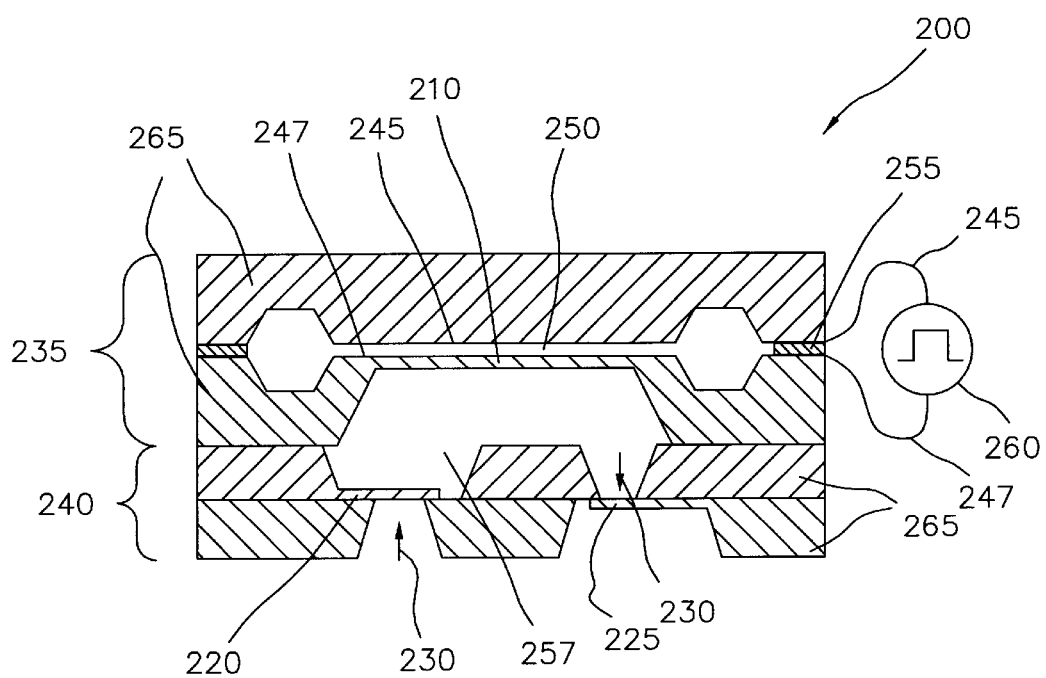
FIG. 5 illustrates a cross-sectional view of a microfluidic pump.

The types of complex devices that are coated by either UNCD or by ceramics using the IBAD deposition process are illustrated by FIGS. 3, 4, and 5. FIG. 3 illustrates a micromachined normally open in-line pressure check valve, generally, 10 having an inlet control element 20 that is supported a distance from above flexible annular member 18, that is preferably comprised of coated silicon with holes 22 for passage of the fluid in the direction 12. An annular substrate 14 having a central orifice 19 therein and having a sealed chamber 16 formed therein, one wall of which being defined by a flexible annular membrane 18. The annular substrate 14 contains first annular projection 15 that together with second annular projection 17 defines chamber 16. An inlet control element 20 is supported by annular projection 21 on the flexible annular membrane 18. It is disposed over the central orifice 19, such that normally a gap 24 is defined between the inlet control element 20 and the central orifice 19 and hence the pressure check valve 10 is open. When the pressure differential, between external pressure and pressure in the chamber 16, exceeds a predetermined threshold, the flexible annular membrane 18 deforms, drawing the inlet control element 20 toward the annular substrate 14 such that the inlet control element 20 seats over the central orifice 19, closing the pressure check valve 10. The operation of pressure check valve 10 is described in detail in U.S. Pat. No. 5,725,017. This device is preferably a part of an implantable microfluidic system involving pumps and control systems. The components are preferably coated with UNCD, although an IBAD coating of alumina is an alternative embodiment.

FIG. 4 illustrates a typical pressure valve 110, generally, containing inlet holes 123 and stops 134. Stops 134 hold the valve lid 120 in position. The fluid flows in direction 112 along the inner circumference of the lower substrate 114. Valve closure is dependent upon fluid flow through pressure valve 110 exerting sufficient force upon valve lid 120 to exceed the deformation force of corrugated flexible diaphragm 118 and the internal pressure of chamber 116. Pressure exerted on valve lid 120 is applied to flexible diaphragm 118 via spacer 131. When sufficient force is applied to valve lid 120, and hence to diaphragm 118, diaphragm 118 flexes and is displaced into chamber 116, thereby drawing valve lid 120 down. Ultimately, if sufficient pressure is applied, valve lid 120 is drawn down to such an extent that valve gap 24 is completely closed. Since valve lid 120 is disposed over holes 122, when valve gap 124 is closed, holes 122 are sealed. See U.S. Pat. No. 5,725,017 for a complete description of this pressure valve.

In this valve, the amount of pressure necessarily applied to valve lid 120 is order for valve 110 to close is determined in part by the pressure within chamber 116. The threshold pressure of valve 110 changes with changing pressure within chamber 116. All of these components are coated in order to assure that the device is impermeable to the environment and to the molecules passing there through. The components are preferably coated with UNCD, although an IBAD coating of alumina is an alternative embodiment.

FIG. 5 illustrates a typical microfluidic pump 200 that is implantable. This pump is comprised of two identifiable units, actuation unit 235 and valve unit 240, which preferably are made of micromachined silicon. Fluid flows in direction 230, entering pump 200 at inlet valve 220 and exiting at outlet valve 225. The components are all comprised of wafers 265. Membrane 210 moves by virtue of drive electrode 245 being electrically charged opposite to electrode 247, which alternately causes membrane 210 to move toward drive electrode 245. Pump driver 260 creates the electrostatic charge. Electrostatic gap 250, which is created by spacers 255, provides room for membrane 210 to move. As membrane 210 moves alternately back and forth, the fluid in chamber 257 is pumped in the direction 230. Membrane 210 is preferably comprised of silicon. The components are preferably coated with UNCD, although an IBAD coating of alumina is an alternative embodiment. See Kovacs for a detailed description of this pump.

Figure 6:
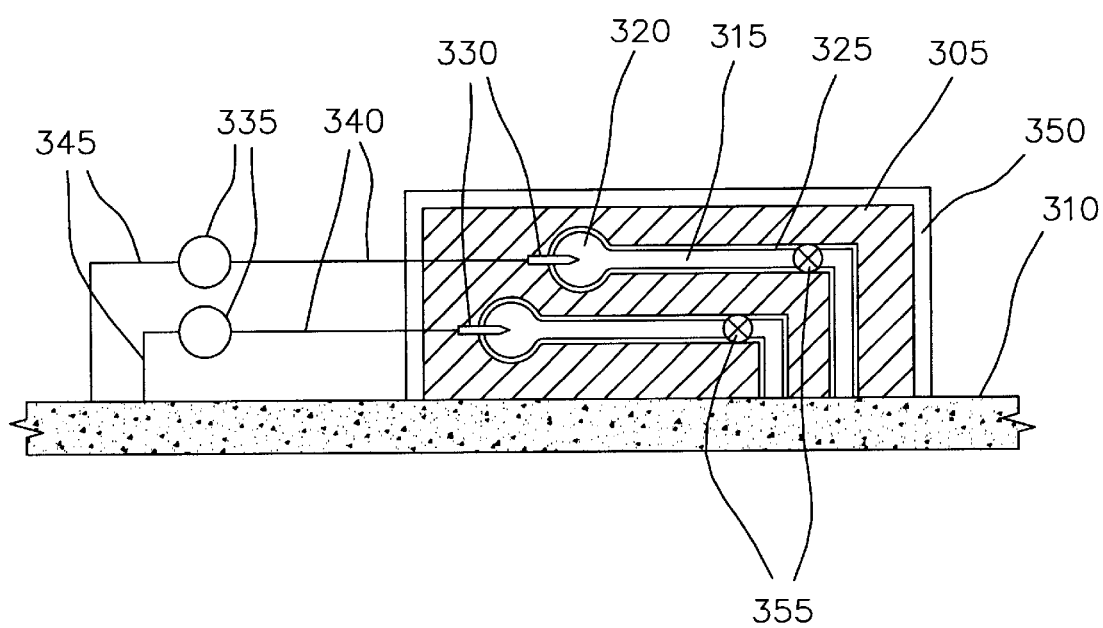
FIG. 6 illustrates a cross-sectional view of an iontophoresis electrode device.

An iontophoresis device 300 is illustrated in FIG. 6. The device 300 may be comprised of silicon that has been processed by known micromachining techniques. The iontophoresis device 300 contains two reservoirs 320 which hold the supply of drugs or other molecules that are to be ejected along channels 315 to the living tissue 310. The drugs or other molecules pass through valves 355 as they pass along channels 315. The iontophoresis device 300 has at least one electrode 330 associated with each reservoir 320. The electrode 330 is charged by electrical signal generator 335 passing an electrical current along lead wire 340, thereby causing the drug or other molecule to be ejected in small amounts from the reservoir 320 and into the channel 315 and into the living tissue 310. The electrical circuit is completed by attaching a ground wire 345 to the living tissue 310.

In one embodiment, the channels are arranged in a matrix for neural stimulation. Such a configuration is preferably used to provide focal stimulation of neural tissue, such as the retina. A retina prosthesis of this type can restore vision by creating pixilated views for the patient by using neurotransmitters as the drug. The drug may preferably be released by passing current through the electrodes 330 or by opening and closing the valves 355.

Compatibility between the iontophoresis device 300 and the drugs or other molecules that are contained therein and that pass from the reservoir 320 and along the channel 315, is achieved by placing a compatible coating 325 on the walls of the device 300. The iontophoresis device 300 itself may also be covered with external coating 350 on its outside with the same coating material or an alternate coating material as that used for coating 325. The coating 325 and external coating 350 are comprised of the same materials and are applied by the same processes previously discussed.

Obviously, many modifications and variations of the present invention are possible in light of the above teachings. It is therefore to be understood that, within the scope of the appended claims, the invention may be practiced otherwise than as specifically described.

What is claimed is:

1. A microfluidic delivery system for the transport of molecules comprising:
    a substrate;
    at least one reservoir in said substrate for containing the molecules;
    a fluid control device controlling release of said molecules from said at least one reservoir; and
    a thin film inert impermeable coating applied to said substrate.
2. The microfluidic delivery system according to claim 1 wherein
    said thin film inert impermeable coating is biocompatible.
3. The microfluidic delivery system according to claim 1 wherein
    the molecules are comprised of at least one drug.
4. The microfluidic delivery system according to claim 1 wherein
    said molecules are ejected by iontophoresis means.
5. The microfluidic delivery system according to claim 1 wherein
    said fluid control device controlling release of said molecules from said at least one reservoir is an electrode.
6. The microfluidic delivery system according to claim 1 wherein
    said thin film inert impermeable coating is comprised of ultra-nanocrystalline diamond.
7. The microfluidic delivery system according to claim 1 wherein
    said thin film inert impermeable coating is comprised of ceramic.

8. The microfluidic delivery system according to claim 7 wherein said ceramic is comprised of silicon oxycarbide.

9. The microfluidic delivery system according to claim 7 wherein said thin film inert impermeable coating is applied by ion-beam assisted deposition.

10. The microfluidic delivery system according to claim 7 wherein said ceramic is comprised of alumina.

11. The microfluidic delivery system according to claim 7 wherein said ceramic is comprised of zirconia.

12. The microfluidic delivery system according to claim 1 wherein said fluid control device is a permeable cap.

13. The microfluidic delivery system according to claim 1 wherein said fluid control device is a disintegrating cap.

14. The microfluidic delivery system according to claim 12 wherein said cap is comprised of electrically conductive ultra-nanocrystalline diamond.

15. The microfluidic delivery system according to claim 1 wherein said fluid control device is a pump.

16. The microfluidic delivery system according to claim 15 wherein said pump is an electrostatic pump.

17. The microfluidic delivery system according to claim 15 wherein said pump is an electromagnetic pump.

18. The microfluidic delivery system according to claim 15 wherein said pump is a pneumatic pump.

19. The microfluidic delivery system according to claim 15 wherein said pump is a piezoelectric pump.

20. The microfluidic delivery system according to claim 1 wherein said fluid control device is a valve.

21. The microfluidic delivery system according to claim 20 wherein said valve is an electrostatic valve or electrostatically controlled valve.

22. The microfluidic delivery system according to claim 20 wherein said valve is an electromagnetic valve or electromagnetically controlled valve.

23. The microfluidic delivery system according to claim 20 wherein said valve is a pneumatic valve or pneumatically controlled valve.

24. The microfluidic delivery system according to claim 20 wherein said valve is a piezoelectric valve.

25. The microfluidic delivery system according to claim 1 wherein said substrate is comprised of silicon.

26. A microfluidic delivery system for the release of molecules comprising:

a substrate;

at least one reservoir in the substrate that is suitable to contain the molecules;

said at least one reservoir having at least one reservoir cap positioned on said reservoir over the molecules;

wherein release of the molecules from said at least one reservoir is controlled by said at least one reservoir cap; and wherein said substrate is coated with a thin film of ultra-nanocrystalline diamond deposited on said microfluidic delivery system wherein said thin film forms a biocompatible impermeably sealed substrate.

27. The microfluidic delivery system according to claim 26 further comprising means for releasing said molecules by diffusion through said at least one reservoir cap.

28. The microfluidic delivery system according to claim 26 further comprising means for releasing said molecules by disintegration of said at least one reservoir cap.

29. The microfluidic delivery system according to claim 26 further comprising means for releasing said molecules by iontophoresis.

30. The microfluidic delivery system according to claim 26 wherein said substrate is comprised of silicon.

31. The microfluidic delivery system according to claim 26 wherein said at least one reservoir cap is comprised of a thin film of ultra-nanocrystalline diamond.

32. The microfluidic delivery system according to claim 31 wherein at least a portion of said ultra-nanocrystalline diamond thin film is electrically conductive.

33. A method of fabricating a microfluidic delivery system for release of molecules having at least one reservoir containing the molecules for release comprising:

providing a substrate;

depositing a thin inert and impermeable film coating;

filling said at least one reservoirs with molecules to be release into living tissue; and capping said at least one reservoirs with a cap material which retains the molecules.

34. The method of claim 33 further comprising forming said thin inert and impermeable film coating from ultra-nanocrystalline diamond.

35. The method of claim 33 further comprising forming said thin inert and impermeable film coating from silicon oxycarbide.

36. The method of claim 33 further comprising applying said thin inert and impermeable film coating by ion-beam assisted deposition.

37. The method of claim 36 wherein said ion-beam assisted deposition coating is comprised of aluminum oxide.

38. The method of claim 33 further comprising the step of forming said substrate from silicon.

39. The method of claim 33 further comprising the step of forming said cap from selectively permeable material to release the molecules.

40. The method of claim 33 further comprising the step of forming said cap from material which disintegrates to release the molecules.

41. The method of claim 33 further comprising the step of forming said cap from ultra-nanocrystalline diamond.

42. The method of claim 33 further comprising the step of forming said cap from silicon oxycarbide.

43. An iontophoresis device for the transport of molecules comprising:
   a substrate;
   at least one reservoir in said substrate for containing the molecules;
   a fluid control device controlling release of said molecules from said at least one reservoir; and
   a thin film inert impermeable coating applied to said substrate.

44. The iontophoresis device according to claim 43 wherein
   said fluid control device is at least one electrode in said at least one reservoir.

45. The iontophoresis device according to claim 43 wherein
   said fluid control device controls the release of said molecules through an array of orifices.

* * * * *